United States Patent [19]
Wynne et al.

[11] Patent Number: 6,165,170
[45] Date of Patent: Dec. 26, 2000

[54] LASER DERMABLATOR AND DERMABLATION

[75] Inventors: James Jeffrey Wynne, Mount Kisco; Stephen Henry Gomory, Tarrytown; Jerome Marvin Felsenstein, Pleasantville, all of N.Y.

[73] Assignee: International Business Machines Corporation, Armonk, N.Y.

[21] Appl. No.: 09/015,875

[22] Filed: Jan. 29, 1998

[51] Int. Cl.[7] .................................................. A61B 18/18
[52] U.S. Cl. .................................... 606/9; 606/10; 606/12
[58] Field of Search ............................. 606/2, 9, 10, 11, 606/12, 14, 15, 16, 17

[56] References Cited

U.S. PATENT DOCUMENTS

| | | |
|---|---|---|
| 3,902,036 | 8/1975 | Zaleckas . |
| 4,215,694 | 8/1980 | Isakov et al. . |
| 4,316,467 | 2/1982 | Muckerheide . |

(List continued on next page.)

FOREIGN PATENT DOCUMENTS

| | | |
|---|---|---|
| 2239773 | 6/1996 | Canada . |
| 0111060A1 | 9/1983 | European Pat. Off. . |
| 0111060 | 6/1984 | European Pat. Off. . |
| 0198959A2 | 10/1986 | European Pat. Off. . |
| 0724866A1 | 1/1996 | European Pat. Off. . |
| 0724866 | 8/1996 | European Pat. Off. . |
| 4026240 | 2/1992 | Germany . |
| 4026240A1 | 2/1992 | Germany . |
| 19521003 | 8/1996 | Germany . |
| 19521003C1 | 8/1996 | Germany . |
| 6238413 | 2/1987 | Japan .............................. G02B 26/10 |
| 2581488 | 6/1992 | Japan .............................. A61B 17/36 |
| 5-15546 | 1/1993 | Japan .............................. A61B 17/36 |
| 5-3927 | 1/1993 | Japan .............................. A61N 5/06 |
| 96/02486 | 6/1996 | WIPO . |
| WO96/28212 | 9/1996 | WIPO . |
| WO9628212 | 9/1996 | WIPO . |

OTHER PUBLICATIONS

IEEE Engineering in Medicine and Biology Magazine, vol. 14, No. 3, May/Jun. 1995, "Total Knee Replacement", T. Kienzle III et al., pp. 301–306.

webmaster@lasersurger.com, Center for Laser Surgery, Oct. 29, 1997, Tutorial for Patients, pp. 1–3, Concepts in Ultrapulse Laser Resurfacing, pp. 1–3, R. Adrian, M.D., F.A.C.P.

Archives of Dermatology, vol. 121, May, 1985, "Ultraviolet–Laser Ablation of Skin", R. Lane et al. pp. 609–617.

Lasers in Surgery and Medicine 6:504–513 (1987), "Ultraviolet Laser Ablation of Skin: Healing Studies and a Thermal Model", R. Lane et al.

(List continued on next page.)

*Primary Examiner*—Linda C. M. Dvorak
*Assistant Examiner*—Roy Gibson
*Attorney, Agent, or Firm*—Wayne L. Ellenbogen

[57] ABSTRACT

A laser system (called a UV Dermablator) and method that enables a clean, precise removal of skin while minimizing collateral damage to the skin underlying the treated region. The depth of ablation can be controlled via feedback from the physiology of the skin, namely the infusion of blood into the area of excision when skin has been ablated to a sufficient depth to produce bleeding. A second laser, such as a uv light source with a different wavelength, to penetrate the blood, heating it sufficiently to coagulate the blood. Other features provide precise control, permitting the epidermis to be removed down to the papillary dermis, following the undulations of the papillary dermis. This lateral and depth control may be accomplished by using careful observation, assisted by spectroscopic detection, to identify when the epidermis has been removed, exposing the underlying dermis, with spatial resolution appropriate for the spacing of the undulations of the papillary dermis. Yet other features which provide a feedback control mechanism which utilizes the optical characteristics such as the color, appearance and remittance of the definable skin layers to control the depth of ablation at each location.

19 Claims, 12 Drawing Sheets

U.S. PATENT DOCUMENTS

| | | |
|---|---|---|
| 4,420,812 | 12/1983 | Ito et al. . |
| 4,784,135 | 11/1988 | Blum et al. . |
| 4,888,708 | 12/1989 | Brantmark et al. . |
| 4,973,848 | 11/1990 | Kolbanov et al. . |
| 5,108,388 | 4/1992 | Trokel . |
| 5,163,933 | 11/1992 | Grundfest . |
| 5,207,576 | 5/1993 | Vassiliadis et al. . |
| 5,290,273 | 3/1994 | Tan . |
| 5,312,396 | 5/1994 | Feld et al. . |
| 5,336,217 | 8/1994 | Buys et al. . |
| 5,350,376 | 9/1994 | Brown .................................... 606/12 |
| 5,405,368 | 4/1995 | Eckhouse . |
| 5,411,502 | 5/1995 | Zair . |
| 5,423,803 | 6/1995 | Tankovitch et al. . |
| 5,435,724 | 7/1995 | Goodman et al. . |
| 5,522,813 | 6/1996 | Trelles . |
| 5,527,350 | 6/1996 | Grove et al. . |
| 5,531,740 | 7/1996 | Black . |
| 5,549,599 | 8/1996 | Sumiya . |
| 5,554,153 | 9/1996 | Costello et al. ......................... 606/11 |
| 5,554,156 | 9/1996 | Shimizu . |
| 5,558,666 | 9/1996 | Dewey et al. . |
| 5,571,151 | 11/1996 | Gregory . |
| 5,582,752 | 12/1996 | Zair . |
| 5,611,795 | 3/1997 | Slatkine et al. . |
| 5,655,547 | 8/1997 | Karni . |
| 5,820,627 | 10/1998 | Rosen et al. ............................. 606/12 |
| 5,839,446 | 11/1998 | Waner et al. ............................ 606/9 |
| 5,843,072 | 12/1998 | Furumoto et al. ..................... 606/9 |
| 5,860,967 | 1/1999 | Zavislan et al. ........................ 606/12 |

OTHER PUBLICATIONS

Reviews of Modern Physics, vol. 14, Apr./Jul. 1942, Electron Transfer Spectra and Their Photochemical Effects, E. Rabinowitch, pp. 112–131.

Journal of the American Academy of Dermatology, Nov. 1997, Clinical and Laboratory Studies, Long–term results after $CO_2$ laser skin resurfacing: a comparison of scanned and pulsed systems, E. Ross et al., pp. 709–718.

IBM Journal of Research and Development, vol. 40, No. 2, Mar. 1996, "An overview of computer–integrated surgery at the IBM T.J. Watson Res. Center", R. Taylor et al., pp. 163–183.

The MIT Press, "Computer–Integrated Surgery, Technology and Clinical Applications", "Multimodal Information for Computer–Integrated Surgery", R. Mosges et al., pp. 5–19, (1996).

1989 Derwent Publications, Ltd., "Photochemical Therapy and Fluorescence Diagnostic Systems".

Vitalase Surgi–Centre Cosmetic Surface Smoothing Erbium: YAG Laser, Nov. 4, 1997, http://www.vitalase.com/erbium.html, "CB Erbium/2.94".

Biophotonics International, May/Jun. 1997, "The Erbium Laser Gains a Role in Cosmetic Surgery", I. Miller, PhD, pp. 38–42.

Lasers in Surgery and Medicine 19: 324–330 (1996), Pulsed Erbium: YAG Laser Ablation in Cutaneous Surgery, R. Kaufmann et al.

Aesthetic Surgery Journal—May/Jun. 1997, "The Erbium: YAG Laser: A Review and Preliminary Report on Resurfacing of the Face, Neck, and Hands", D. McDaniel et al., pp. 157–162.

"The Erbium YAG Laser System", K. Khatri et al., 3 pages, (Dec. 1996).

"Evaluating Competitive Erbium YAG Laser Systems", 1 page.

"Erbium Laser Treatment Techniques", Table, 1 page.

"Laser Cosmetic Surgery: Separate the Reality From the Hype", C. Guttman.

Skin & Allergy News, Nov. 1997, "Dermatologists Give Er:YAG Laser Mixed Reviews", B. Bates, p. 42.

Dermatology Times, Sep. 1997, "Addressing Complications from Laser Resurfacing", A. Bowser, p. 50.

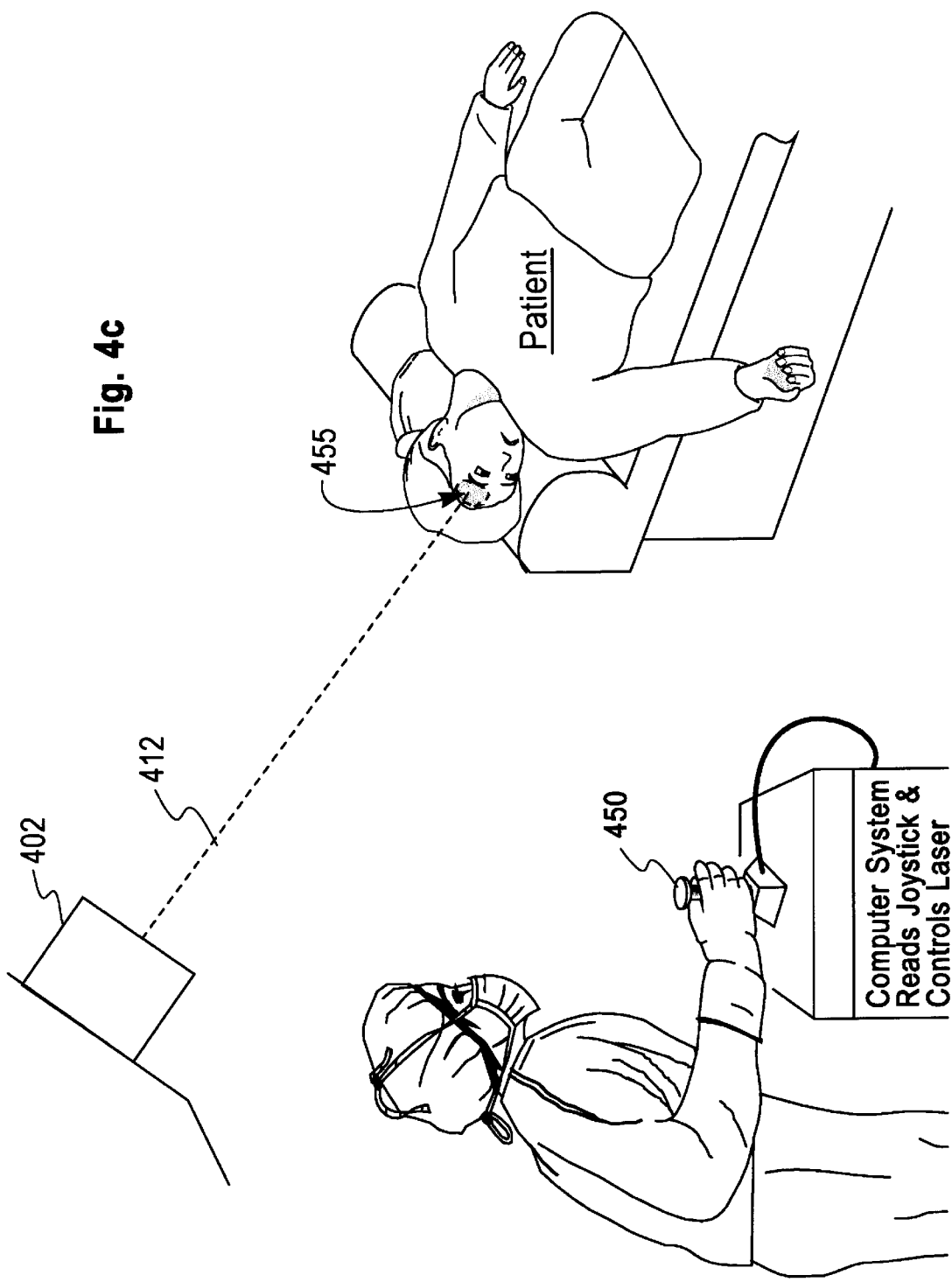

LASER DERMABLATOR AND DERMABLATION

BACKGROUND

Skin problems are pervasive in society. People suffer from conditions ranging from the cosmetic, such as benign discoloration, to fatal ailments, such as malignant melanomas. Treatments range from cosmetic "cover-up" makeup to surgical excision.

In particular, the removal (or "skin peel") of an outer layer of skin is used to treat conditions such as acne, age spots (superficial regions of excess melanin), shallow lesions (e.g. actinic keratoses), and aged skin. FIG. 1 depicts a cross section of normal human skin. The depth of the outer layer, or epidermis, varies, with ranges typically from 50–150 $\mu$m in thickness. The epidermis is separated from the underlying corium (dermis) by a germinative layer of columnar basal cells. The epidermal/dermal interface is characterized by undulations. The basal cells produce a continuing supply of keratinocytes, which are the microscopic components of the epidermis. Specialized cells called melanocytes, also reside in the basal cell layer and produce the pigment melanin. Although some of the melanin migrates toward the surface of the skin with the keratinocytes, the greatest concentration of melanin remains in the basal cell layer. The uppermost layer of the dermis, which is adjacent to the basal cell layer, is known as the papillary dermis, and the papillae range in width from 25–100 $\mu$m, separated by rete ridges ("valleys") of comparable width.

Removal of the epidermis eliminates superficial sun damage, including keratoses, lentigenes, and fine wrinkling. Removal of the most superficial portions of the dermis, i.e. the uppermost papillary dermis, eliminates solar elastosis and ameliorates wrinkling, with little or no scarring.

One treatment that is currently very popular uses a short pulse carbon dioxide ($CO_2$) laser to coagulate a layer of skin to a depth of ~50–100 $\mu$m /pulse. This treatment is sometimes referred to as a "laser peel." $CO_2$ laser radiation (in the 9–11 $\mu$m region of the infrared) is strongly absorbed by water (contained in all tissue). When the energy/unit volume absorbed by the tissue is sufficient to vaporize the water, a microscopically thin layer of tissue at the surface of the irradiated region is rendered necrotic; (see e.g., R. M. Adrian, "Concepts in Ultrapulse Laser Resurfacing," URL—http://www.lasersurgery.com/physicians.html (1996)). The skin is coagulated on the surface of the region irradiated by the infrared beam from the $CO_2$ laser. After irradiation, the dehydrated, necrotic surface layer is mechanically removed, and additional irradiation takes place, this process being repeated until the desired depth of tissue is removed. In medical terms, tissue is removed with less collateral damage than with other modalities, e.g., liquid nitrogen, cautery, chemical peels; (see e.g., E. V. Ross et al, "Long-term results after $CO_2$ laser skin resurfacing: a comparison of scanned and pulsed systems," J Amer Acad Dermatology 37: 709–718 (1997)).

The radiation features that result in reduced collateral damage are: a wavelength that is strongly (optically) absorbed; and a pulse duration that is short compared to the time for deposited energy to diffuse into the surrounding tissue; (see e.g., R. J. Lane, J. J. Wynne, and R. G. Geronemus, "Ultraviolet Laser Ablation of Skin: Healing Studies and a Thermal Model," Lasers in Surgery and Medicine 6: 504–513 (1987)). The short pulse $CO_2$ laser, with an absorption coefficient in tissue of ~1/50 $\mu m^{-1}$ and a pulse duration of ~10–100 ns, leads to a reduction of collateral damage as compared to a continuous wave (cw) $CO_2$ laser or lasers at other visible and near infrared wavelengths. But clinical results on patients treated for the elimination of wrinkles with the short pulse $CO_2$ laser show an abundance of undesirable aftereffects, including erythema (red, inflamed skin) and crusting, with the possible formation of scar tissue and dyspigmentation. (see e.g., Andrew Bowser, "Addressing Complications from Laser Resurfacing-Deep scarring and insufficient follow-up are among causes cited," Dermatology Times 18, No. 9: 50–51 (September 1997)). One problem with the pulsed $CO_2$ laser is that the radiation absorption depth is not shallow enough. Another is the deposited laser energy is not sufficiently removed from the surface to completely prevent collateral damage. As a result, this modality for "superficial skin peel" can be relatively painful, often requiring general anesthesia and a prolonged recovery period.

A newer treatment that is gaining in popularity uses a pulsed erbium YAG (Er:YAG) laser, emitting radiation at 2.94 $\mu$m in the infrared, where water absorption is even stronger than at $CO_2$ wavelengths. Er:YAG light is approximately 10 times more strongly absorbed in skin than $CO_2$ laser light. When compared to the effect of $CO_2$ laser irradiation, a shallower layer of skin absorbs the radiation and is vaporized and ablated from the surface, leaving a thinner thermally damaged and coagulated layer adjacent to the removed tissue. Damage has not been observed to exceed a depth of ~50 $\mu$m of collagen denaturation. (See e.g., R. Kaufmann and R. Hibst, "Pulsed Erbium:YAG Laser Ablation in Cutaneous Surgery," Lasers in Surgery and Medicine 19: 324–330(1996)).

Treatment with the Er:YAG laser rejuvenates skin, with less pain, less inflammation, and more rapid healing than treatment with the $CO_2$ laser. The depth of penetration with the Er:YAG laser, being shallower, does not thermally stimulate new collagen growth as much as the $CO_2$ laser, so fine wrinkles are not eradicated as effectively. Dermatologists and cosmetic surgeons are finding the Er:YAG laser preferable for younger patients who have superficial skin damage but less wrinkling, while the $CO_2$ laser is thought to be preferable for older patients who want to have fine wrinkles removed around the lips and the eyes (see e.g., Betsy Bates, "Dermatologists Give Er:YAG Laser Mixed Reviews," Skin & Allergy News 28, No. 11: 42 (November 1997)). Although the depth of penetration is shallower and the skin is actually ablated rather than just rendered necrotic, the ablation depth and the depth of coagulated skin limits the precision with which the Er:YAG can remove epidermal tissue without damaging the underlying papillary dermis. And while pain is lessened, many patients still require some sort of anesthesia during treatment and the application of a topical antibiotic/antimicrobial agent following treatment to prevent infection during healing.

It is also generally known in the art to use ultraviolet wavelength lasers for medical and dental applications. See e.g., U.S. Pat. No. 4,784,135, issued Nov. 15, 1988, entitled "Far Ultraviolet Surgical and Dental Procedures," by Blum, Srinivasan, and Wynne. See also U.S. Pat. No. 5,435,724, entitled "Dental Procedures and Apparatus Using Pulsed Ultraviolet radiation," issued Jul. 25, 1995 to Goodman, Wynne, Kaufman and Jacobs.

The need remains for an apparatus and method which provides for skin resurfacing in a painless environment with exquisite control and markedly decreased morbidity by eliminating erythema and scarring. There is also a need for an apparatus and method of using ultraviolet (uv) light, delivered in a finely-controlled, countable number of short pulses with sufficient fluence to ablate skin, to remove thin layers of skin at the site of irradiation, with exquisite lateral precision and depth control, resulting in minimal damage to the skin surrounding and underlying the ablated area. The present invention addresses these needs.

There is also a need for an apparatus and process which enables a controlled removal of the epidermis down to the papillary dermis, adapting to the undulations of the papillary dermis. The present invention addresses such a need.

SUMMARY

In accordance with the aforementioned needs, the present invention is directed to a system (called a Dermablator) that can be used to carry out an improved "laser peel" of the skin. The present invention is also directed to a process, Dermablation, that leads to clean, precise removal of surface skin while minimizing collateral damage to the skin underlying the treated region.

An example of a surgical system for removing skin having features of the present invention includes: a pulsed light source capable of delivering a fluence F exceeding an ablation threshold fluence $F_{th}$; and a control mechanism, coupled to the light source, for directing light from the light source to locations on the skin and determining if a skin location has been ablated to a desired depth.

The light source is preferably a laser, for example: an argon fluoride (ArF) laser having a wavelength of approximately 193 nm; a krypton fluoride (KrF) laser having a wavelength of approximately 248 nm; a xenon chloride (XeCl) laser having a wavelength of approximately 308 nm; a xenon fluoride (XeF) laser having a wavelength of approximately 351 nm; or an Er:YAG laser.

The present invention has other features which limit the depth of ablation by utilizing feedback from the physiology of the skin, namely the infusion of blood into the area of excision when skin has been ablated to a sufficient depth to produce bleeding. The infusion of blood can act as a "stop" to prevent further ablation, thereby effectively terminating the dermablation. The blood can then be removed by washing it away with physiological saline solution, clearing the area for further treatment.

One version of the present invention utilizes a laser having a relatively low blood absorption characteristic, such as an ArF laser, to ablate the skin to a sufficient depth to produce bleeding. A second laser, such as a uv light source with a different wavelength and a relatively high blood absorption characteristic, is then utilized to penetrate the blood, heating it sufficiently to coagulate the blood, stemming subsequent bleeding, yet leaving the tissue with an intact ability to heal without the formation of scar tissue.

An example of such a system, wherein the laser is an ArF laser, further comprises: a coagulating light source having a different wavelength than the ArF laser and a relatively high blood absorption characteristic; means for detecting the appearance of blood at a given skin location; and means for switching to the coagulating light source, in response to the detection of blood at a given skin location.

Examples of the coagulating light source include a krypton fluoride (KrF) laser having a wavelength of approximately 248 nm; a xenon chloride (XeCl) laser having a wavelength of approximately 308 nm; and a xenon fluoride (XeF) laser having a wavelength of approximately 351 nm.

The present invention has still other features which provide precise lateral and depth control, permitting the epidermis to be removed down to the papillary dermis, following the undulations of the papillary dermis, so that the papillae are not penetrated even though the epidermis is removed in the adjacent rete ridges. This lateral and depth control may be accomplished by using careful observation, assisted by spectroscopic detection, to identify when the epidermis has been removed, exposing the underlying dermis, with spatial resolution appropriate for the spacing of the undulations of the papillary dermis.

The lateral and depth control of the present invention is one advantage over prior art laser peels operating at wavelengths which lead to thermal damage in the tissue underlying the ablated region that renders this underlying tissue denatured and coagulated. For example, the use of current $CO_2$ lasers make it difficult if not impossible to determine how deep the ablation has penetrated based on real-time observation and/or feedback control.

Accordingly, the present invention has yet other features which provide a feedback control mechanism which utilizes the optical characteristics such as the color, appearance and remittance of the definable skin layers. Using ultraviolet light ablation, the tissue underlying the ablated region will retain its undamaged morphology and color, permitting real-time determination of whether the ablation has proceeded to the correct depth, e.g., to or just beyond the epidermal-dermal interface.

Another example of the present invention includes a means for controllably abalating the skin by detecting a color change near or at the epidermal/dermal boundary. The control mechanism could be a feedback control mechanism, comprising: a second light source illuminating the skin; and at least one photodetector having an input and an output; the input receiving scattered/reflected/fluoresced light from the second light source, and the output providing a feedback signal to the system causing the light source to be inhibited at a given location, in response to the second light source at the input. Examples of the second light source include a visible light source; an infrared light source; and an ambient light source. Another example of the second light source is one which is both relatively highly absorbed by epidermal melanin and relatively highly remitted by a dermal layer.

Furthermore, the present invention has features that serve to automate the removal of skin, wherein the ablating laser beam can be scanned accurately and repeatably over a designated area of skin under the control of a computer system which utilizes real-time observation and/or feedback to control the depth of ablation at each location. The areas to be scanned may be designated by an adjunct visible alignment laser, employing an input device to scan the alignment beam over the area of skin to be treated and recording the beam positions for subsequent automatic scan of the ablating laser beam over the same scan domain. Alternatively, the area of treatment may be specified by recording its image with a camera and designating on the digital image the locations to be treated.

An example of an automated system having features of the present invention includes an alignment and recording mechanism, comprising: a visible laser emitting a beam illuminating the skin at a location coincident with the ablating light; means for scanning the beam across the locations on the skin; and means for recording scanned beam positions, coupled to the means for scanning, for subsequent automatic scan of an ablating light source across the locations on the skin.

An example of the computer and control mechanism includes: one or more rotatable mirrors, the mirrors positioned in the light source path for controllably scanning the light source; one or more motors, coupled to the mirrors, for angularly rotating and feeding back angular positions of the one or more mirrors; and a computer, coupled to the light source and the motors for controlling the motors and selectively shuttering the light source at a given location on the skin.

In yet another example, the computer includes a feedback control system, coupled to the light source for selectively shuttering the light source at a given location on the skin. The shuttering mechanism could be an active mask array, coupled to the feedback control system, for selectively shuttering the light source at a given location that has been ablated to the desired depth.

Still another example of the present invention is a robot/laser system, further including a camera for visualizing an image of the locations on the skin; a computer, coupled to the camera, the computer having an output for displaying and an input for designating the locations of the skin to which the laser is directed.

Preferably, the robot/laser system further includes: one or more rotatable mirrors, the mirrors positioned in the light source path for controllably scanning the light source; one or more motors, coupled to the mirrors, for angularly rotating and feeding back angular positions of the one or more mirrors; a second light source illuminating the skin being ablated, wherein light from the second light source is scattered/reflected/fluoresced from the ablated location; a photodetector having an input and an output; the input for receiving the light from the second light source; and the output coupled to the system and providing a feedback signal to the system for inhibiting the pulsed light source at a given location.

Preferably the robot/laser system includes a registration mechanism for relating coordinates of a point in one patient coordinate frame of reference to a corresponding position in the robot/laser frame of reference. An example of the registration mechanism includes means for attaching fiducials to the skin; a movable tracking laser, coupled to the computer, for recording 3D coordinates of the fiducials; and triangulation means, for establishing 3D locations of the fiducials in the tracking laser frame of reference. Another example of the registration mechanism comprises: means for relating points corresponding to an area of skin in the patient frame of reference subsequent to a change in position, to the same area of skin in a patient frame of reference prior to said change in position. Yet another example of the registration mechanism comprises means for accurately directing the light source by relating points on an area of skin defined in a digital image, to an area of skin on the patient.

An alternative registration mechanism comprises: means for attaching fiducials to the skin; a pair of cameras, coupled to the computer and mounted at fixed positions relative to the robot/laser system for recording coordinates of the fiducials; calibration means for relating the fixed positions of the cameras to the robot/laser system from a predetermined calibration transformation; and a camera model for mapping the relationship between each location in 2D camera images and a set of 3D points in an imaged space that map to it.

Another example a robot/laser system of the present invention includes: a camera for visualizing an image of the locations on the skin; a computer, coupled to the camera, the computer having an output for displaying and an input for designating the locations of the skin to which the laser is directed; a flexible optical fiber bundle having an output end and an input end, the output end being attached to a mask for affixing to the patient and the input end adapted for receiving the light source in a predetermined manner; and a removable mirror located adjacent to the input end for viewing the skin through the fiber bundle using the camera.

In addition to serving to remove cosmetic defects, i.e. seborrheic keratoses and lentigenes, the Dermablator/Dermablation can provide a modality to treat other pathologies of the epidermis, including Bowen's disease, exophytic warts, flat warts, lichen-planus-like keratosis (LPLK), and actinic keratoses. Thus, this invention provides an apparatus and process for treating a wide range of common skin conditions.

Furthermore, there are many other applications of this invention: (i) The precise superficial capability of Dermablation allows tissue to be "marked," i.e., scored with an identifying mark, either on the patient or on biopsy samples; (ii) Localized fungal infection of the toenail may be treated by ablating the infected region to the desired depth without damaging underlying tissue; (iii) Burn eschar (the result of a serious burn) may be removed by ablating it with the Dermablator, following the variable thickness of the eschar and stopping at each location as soon as healthy, viable tissue is uncovered; (iv) Malignant melanoma may be removed by Dermablation with elimination of surgically-induced metastasis, i.e., no viable cancer cells will be released into the patient's system; (v) Patients with bacterial or viral infection (e.g., AIDS) may be treated with no danger that the tissue ablated from the surface will contain viable viral particles or other microbes, since Dermablation decomposes the ablated material into small inert molecular or atomic fragments; (vi) Patients with the rare condition of Epidermolysis Bullosa, whose delicate skin is incapable of repairing itself following even minor surface cuts and wounds, can have epidermal lesions removed by Dermablation without compromising their fragile dermis; and (vii) Eyelid lesions at the tarsal margin, such as hydrocystoma and Chalazion (sty), may be treated with great precision, resulting in minimal damage to the eyelashes and minimizing the likelihood of notches or other depressions in the tarsal margin that can interfere with tear flow and mucous distribution on the inner surface of the eyelid.

An additional application is to use Dermablation to remove a basal cell carcinoma. Here, the lesion can be selectively marked with an exogenous agent that provides contrast between the lesion and surrounding healthy tissue. Basal cell carcinomas are differentiated from surrounding tissue in biopsy specimens by standard histological treatment, i.e., staining the tissue with chemicals. Such histology is used to make the diagnosis of basal cell carcinoma in the biopsy. Staining agents can be applied directly on the patient, providing a visible differentiation of the basal cell carcinoma, such differentiation being used to guide the Dermablator to remove the lesion with minimal collateral damage.

BRIEF DESCRIPTION OF THE DRAWINGS

These and other features and advantages of the present invention will become apparent to one of ordinary skill in the art by reference to the attached detailed description with reference to the accompanying drawings, wherein:

FIG. 4C depicts a form of the apparatus including the surgeon interacting with the patient via a remote mechanism in accordance with the present invention;

DETAILED DESCRIPTION

By way of overview, UV light removes thin layers of tissue at a rate that depends on the fluence F of the light. There is a threshold fluence $F_{th}$, and areas at the surface of the tissue that are irradiated with a F exceeding $F_{th}$ are ablated to a depth of approximately 1 μm for each (short) pulse of light. The unablated tissue underlying and adjacent to the ablated area absorbs some light and is damaged to a depth of somewhat less than 1 μm, essentially to sub-cellular depth. Successive light pulses remove additional thin, layers, and after the last pulse there is only an ultra-thin, sub-cellular layer of tissue at the margins of the ablated region that experiences damage. Thus, collateral damage is intrinsically minimized. The surgeon or medical practitioner needs a source of light delivering $F>F_{th}$ and a delivery tool. The source might be a far UV pulsed laser, such as an excimer laser. Different excimer lasers emit radiation at different wavelengths, which ablate tissue to different depths and with different $F_{th}$. Well-known far uv excimer laser systems include XeF at 351 nm, XeCl at 308 nm, KrF at 248 nm, and ArF at 193 nm. All excimer laser systems have been shown to be capable of emitting pulses of far uv light that exceed ablation threshold for human (and animal) tissue, including skin.

Figure 2:
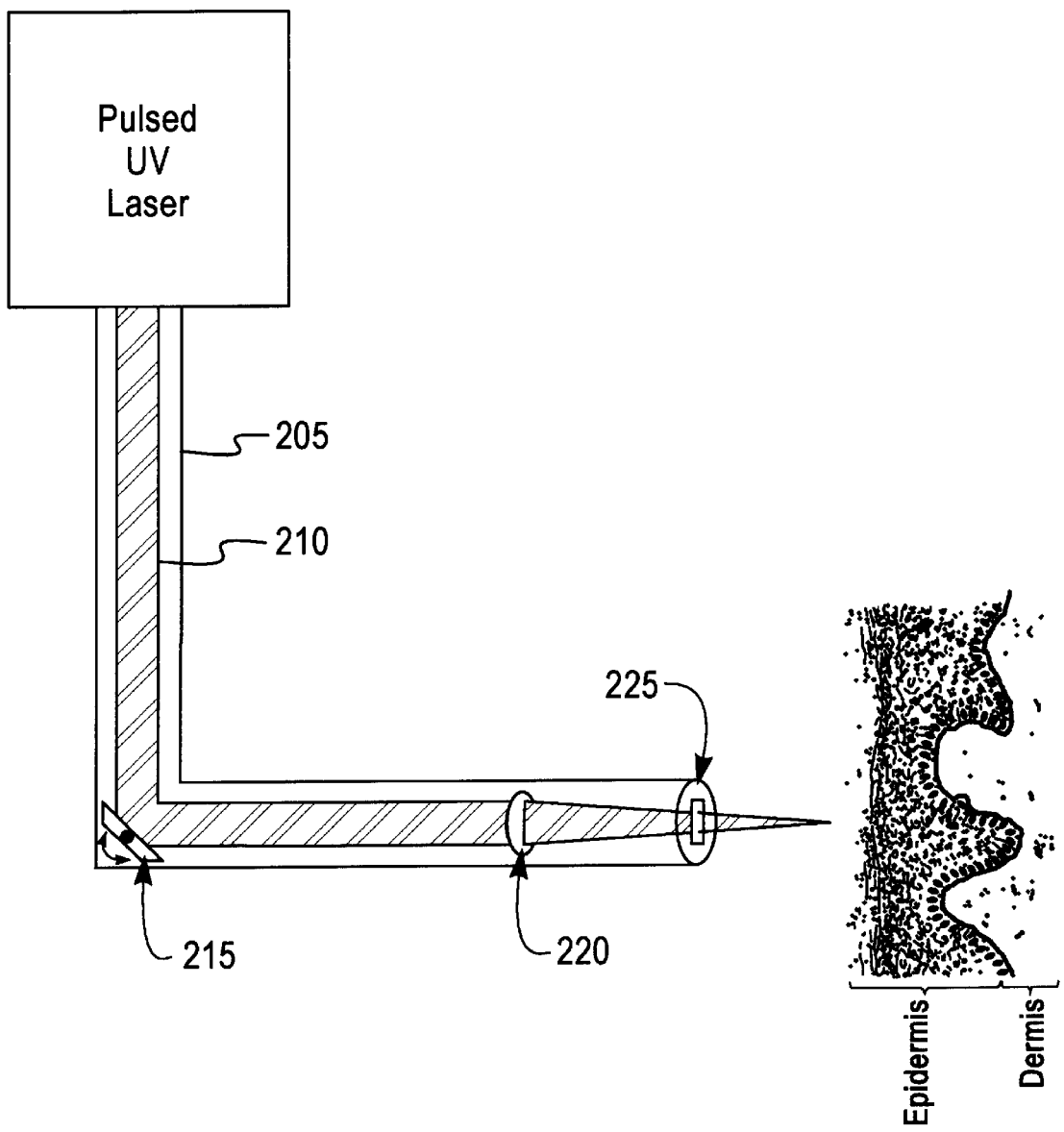
FIG. 2 depicts a form of the apparatus constructed in accordance with the present invention.

FIG. 2 depicts an example of an apparatus having features of the present invention. As depicted, the delivery tool might be a "pipe" 205 through which the light beam 210 is transmitted from source to tissue, with an adjustable steering mirror 215 to direct the beam around corners and an adjustable lens/masking system, such as lens 220 and slit 225 at the delivery end, to shape the light beam into the desired pattern where it irradiates the tissue.

Figure 3:
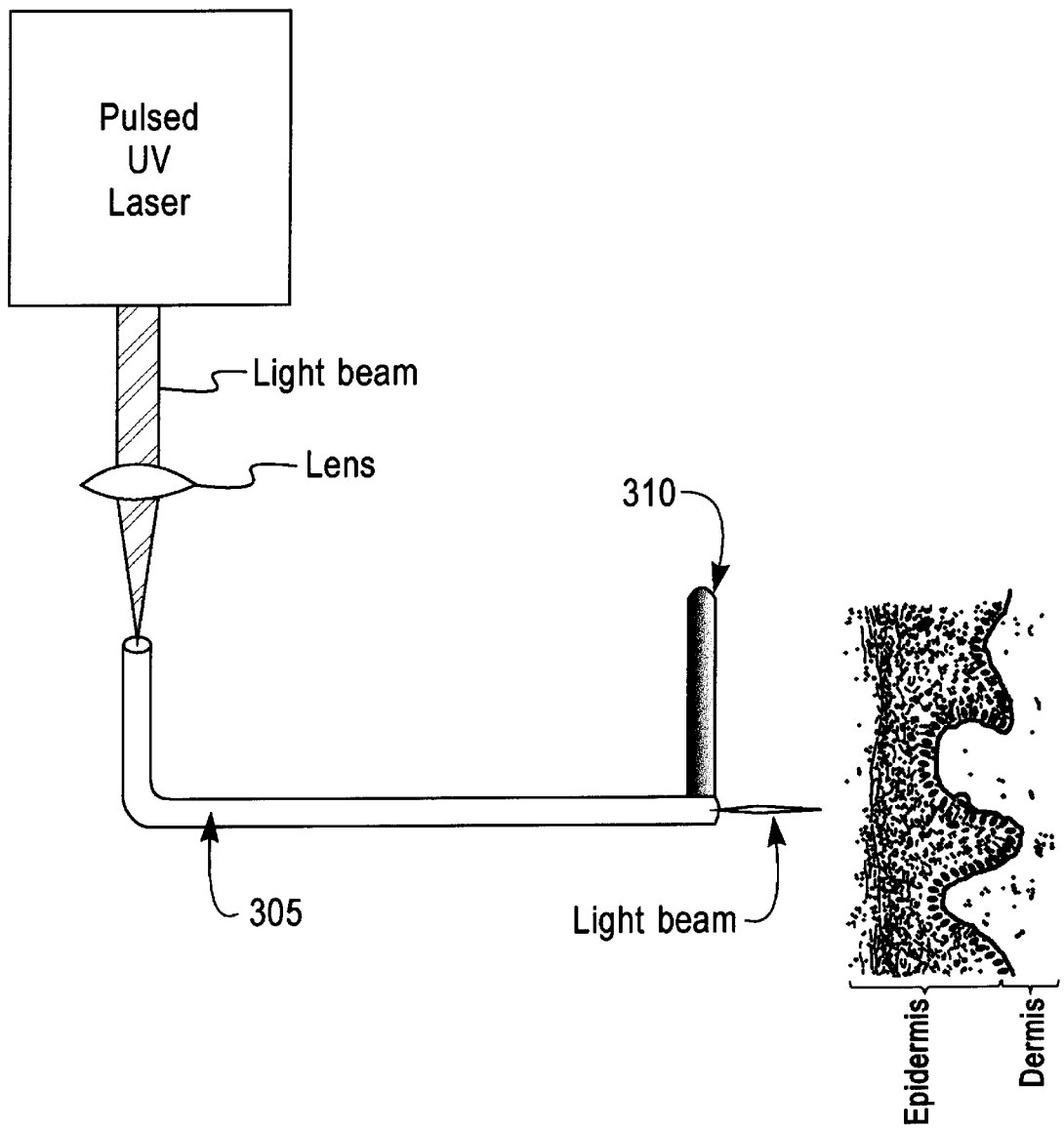
FIG. 3 depicts a form of the apparatus constructed in accordance with the present invention.

FIG. 3 depicts another example of an apparatus having features of the present invention. As depicted, the delivery tool might be an optical fiber, or a fiber bundle 305 terminated by a hand-held tool 310 that the physician or technician can manipulate to deliver the light beam to the skin area to be irradiated.

Figure 1:
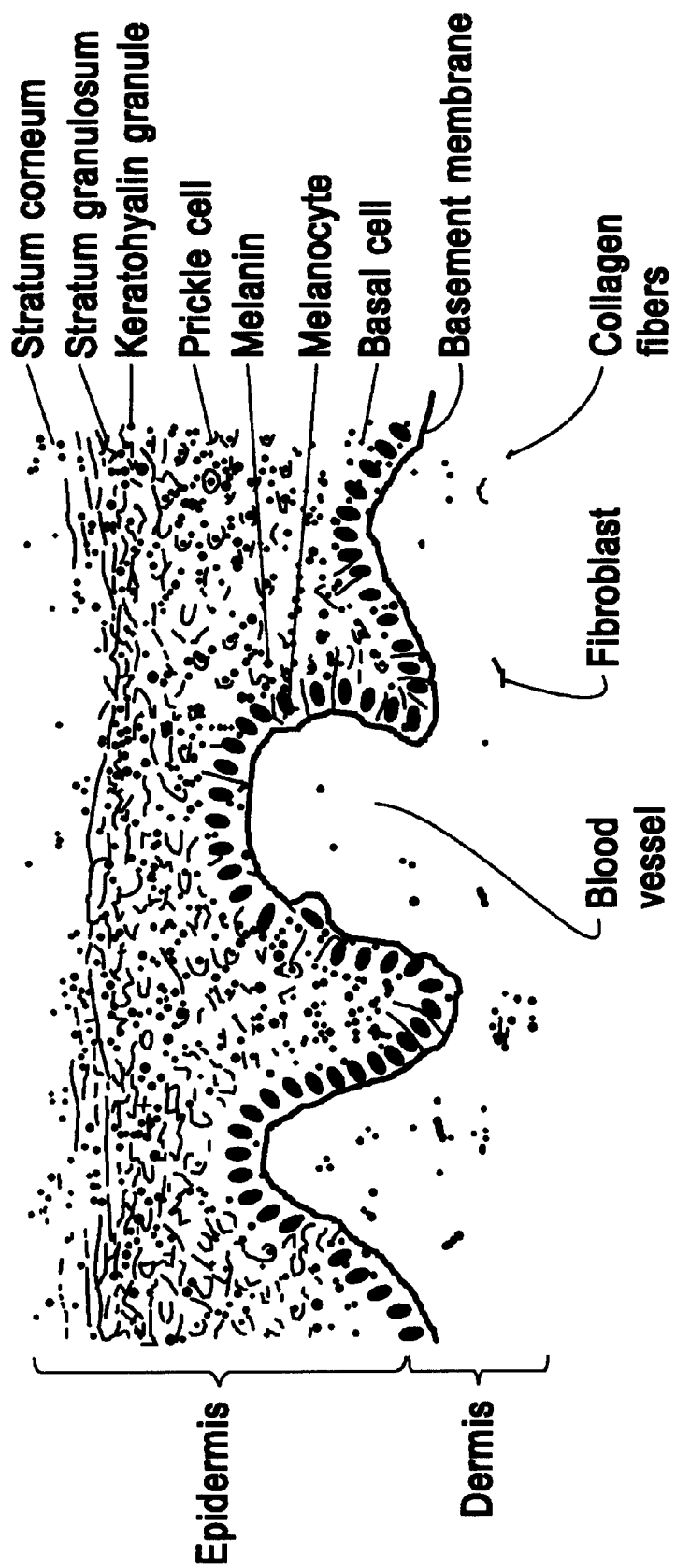
FIG. 1 depicts an cross section of normal human skin.

Referring now to FIGS. 1 and 2, the delivery tool of FIG. 2 can be adjusted to focus the uv irradiation beam to an area small in comparison to the cross-sectional area of a rete ridge of the epidermis. Then the beam can irradiate the area until the epidermis is completely removed, before the beam is scanned/displaced to an adjacent area where the procedure is repeated, ablating this new area of epidermis down to the dermis. In this way the contours of the irregular epidermal/dermal interface can be taken into account. By scanning the uv laser beam across an area of skin in this manner, only epidermis will be removed, with depth precision that mirrors the contours of the papillae of the papillary dermis.

As will be discussed in more detail below, one aspect of the present invention employs a unique detection scheme to enable a precisely contoured removal of tissue. The epidermis has melanin and thereby is colored, whereas the dermis is white. For example, the medical practitioner can watch the ablated site for the appearance of white dermal tissue. Alternatively, a feedback control mechanism such as a photodetector mounted near the delivery end of the laser tool can detect the first appearance of white tissue at the site of irradiation, sending a signal that automatically causes the laser beam to be displaced to the adjacent area, or causing the laser beam to be inhibited or blocked/shuttered until the site of irradiation is displaced to an adjacent area. The photodetector can use ambient light to see the spectroscopic/brightness difference between light scattered from the surface of the dermis in comparison to light scattered from the surface of the pigmented epidermal tissue. The photodetector can employ an appropriate filter to detect a change in spectral shape (as opposed to brightness) when the dermis is unveiled. In another example, the site of irradiation can be illuminated by a low power, visible or infrared beam of light that is scattered from the surface of the skin. When the dermis is unveiled, the scattering will change in intensity, providing a signature for the detector that can be used to scan or shutter the laser beam.

Figure 4A:
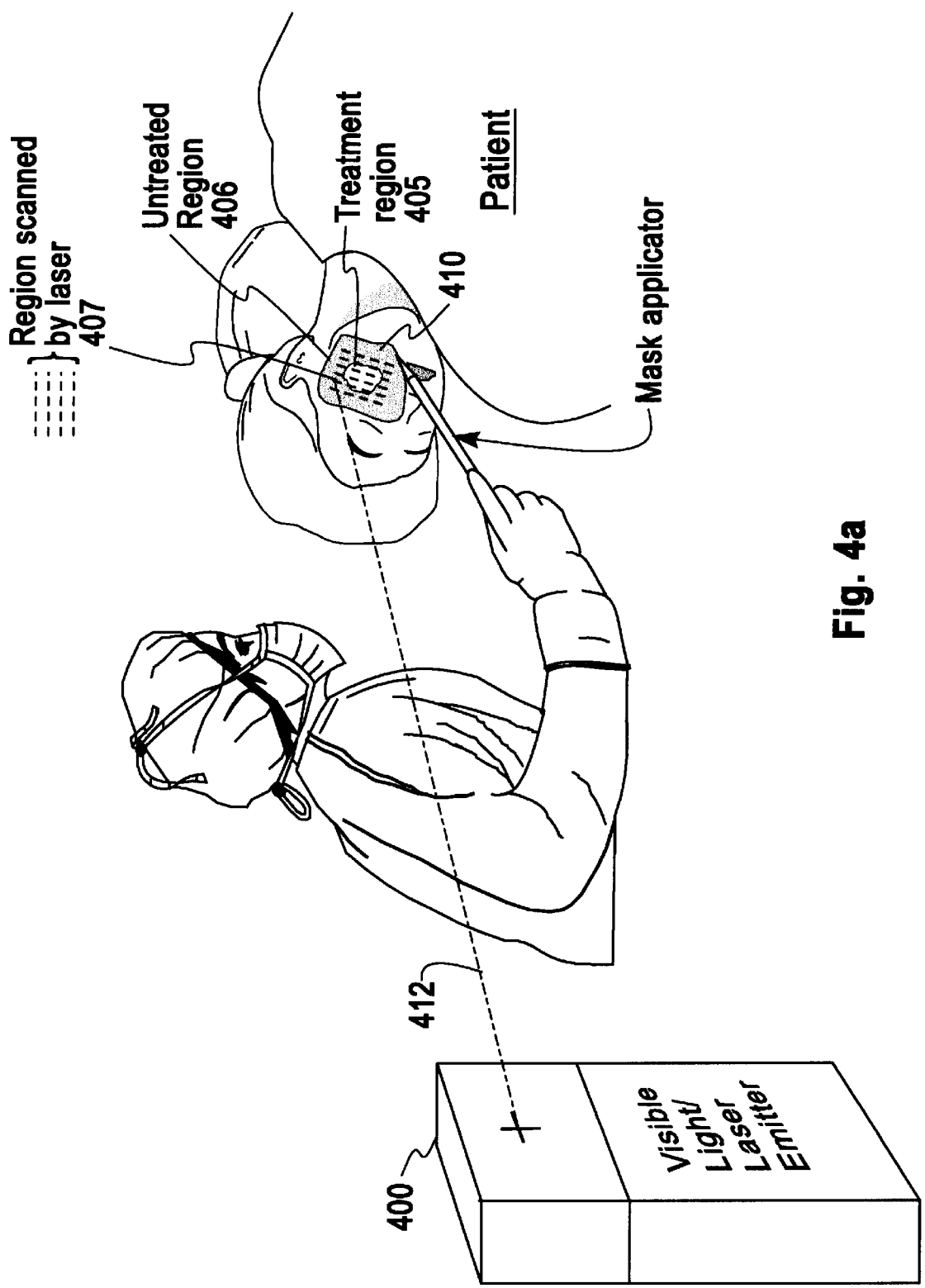
FIG. 4A depicts a form of the apparatus including the surgeon interacting directly with the patient in accordance with the present invention.

As depicted in FIG. 4A, the skin to be irradiated 405 can also be defined by covering the area with a masking material that blocks/absorbs/reflects radiation except at the desired location for the tissue ablation. The masking material 410 could even be made of an erodable material and fabricated with variable thickness, so that a homogenous light beam erodes away the material and ablates skin under the mask only after it has eroded entirely through the mask. Thus, different areas of tissue would receive different "doses" of radiation, producing areas of treated skin with the depth of the ablation controlled by the careful fabrication of the erodable mask. The mask could be impregnated with a marker material, e.g., a fluorescent dye, that would give a clearly recognizable signal when the mask was being eroded, such signal ceasing as soon as the mask was entirely eroded through. Alternatively, the "masking" could be accomplished by applying a "sunscreen" cream or ointment, e.g. zinc oxide, to cover areas where tissue ablation is not wanted. This sunscreen would have to be of sufficient thickness so that it is not completely eroded through to the underlying skin during the treatment.

Figure 4B:
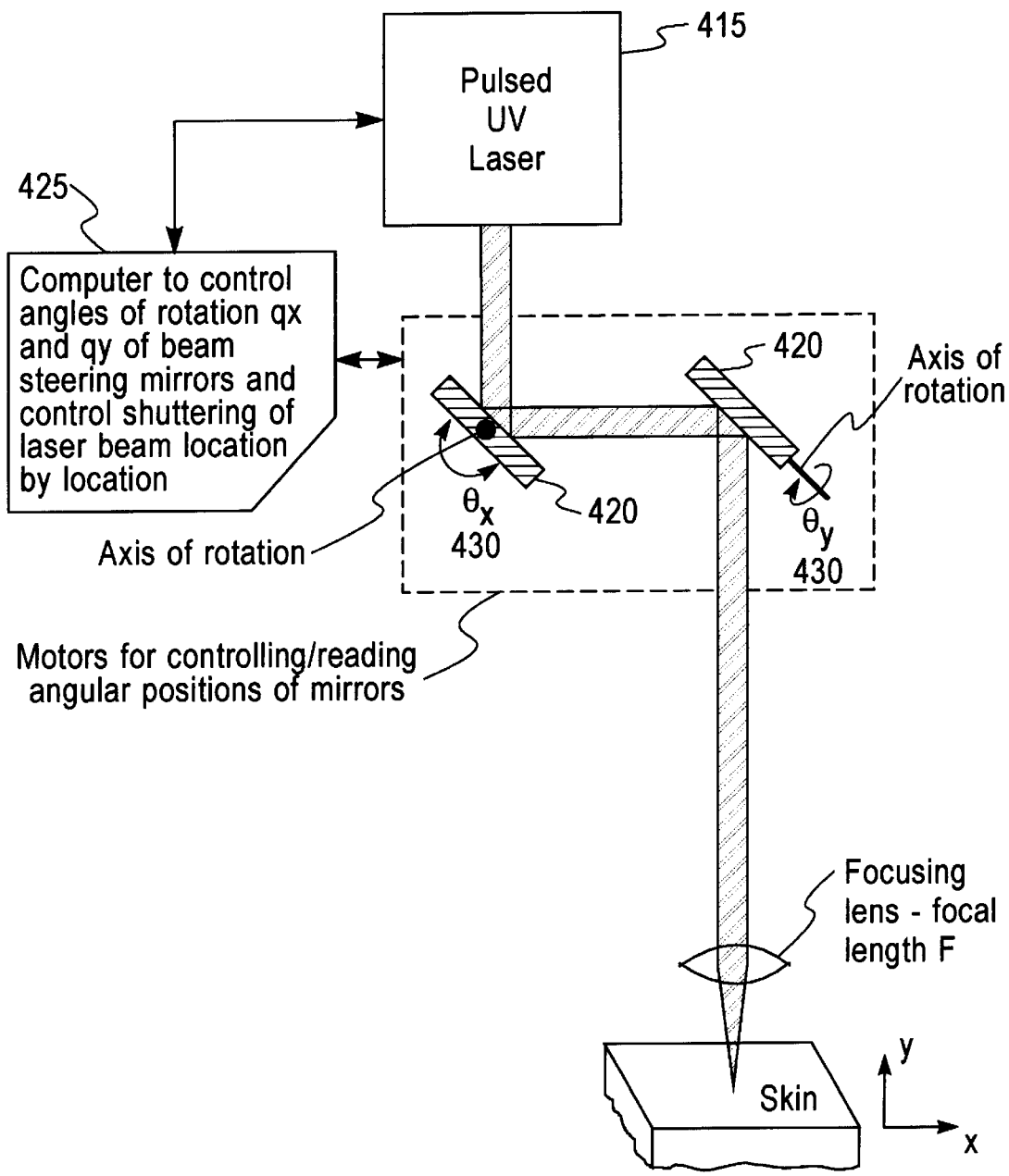
FIG. 4B depicts a form of the apparatus including a means of scanning the laser beam in accordance with the present invention.

A robot/laser system can serve to scan an ablating laser beam to deliver a precisely controlled number of pulses to each location on the area of skin being irradiated. FIG. 4B depicts an example of such a robot/laser system having features of the present invention. The analogy is to a raster scan of an electron beam in a cathode ray tube (TV) display. The amount of energy, or number of pulses, delivered during one scan (or pass) of the laser beam is small enough so that an appropriate dose can be applied to each location by varying the number of times the area is scanned. In contrast, for enhanced speed of tissue removal, one could initially deliver a larger amount of energy per scan, sacrificing precision of depth control, and getting close to the desired depth. Then, successive scans could be carried out at progressively less laser energy, providing increased precision of depth control and allowing the surgeon the fine control to zero in on the desired depth of tissue removal. Whether the surgeon chooses to vary the laser energy or not between scans, one scan could consist of one laser pulse for each location of irradiated tissue or many pulses for each location, the number of pulses being selected to remove tissue to a desired depth. One example is a stationary laser 415 emitting a beam that is guided by a computer-controlled mechanism.

As depicted, one such mechanism could be a pair of mirrors 420 rotating on axes at right angles to one another. The mirrors could be controlled by motors (not shown) having position encoders that enable precise, digital designation of the mirror angles of rotation 430. The motors can be controlled through a standard A/D, D/A circuitry interfaced with a computer 425 running standard servo-control software. The motor encoder information provides the necessary positioning information for fine control. This system is preferably engineered to be capable of accurate positioning of the laser beam on the skin to within 25 μm at a typical target distance of 0.5 m. The control scheme, encoders, motors, mechanical accuracy, and distance from target all affect the overall precision. We assume that the robot has been calibrated, and the forward and inverse kinematics are known with sufficient precision to meet these accuracy requirements.

The system (examples of which are described below) is preferably capable of positioning the laser beam with the required precision at any location on the (irregular) surface of the skin. The surgeon can set the area scanned by the laser by using several possible techniques. For example, the surgeon can affix a physical mask or plate on the robot/laser system that restricts the range of mirror angles for which the beam escapes the laser device. Alternatively, the surgeon could set the extent of the range of the mirror angles by interacting with the controller software through a user input device such as a keyboard, mouse, or joystick. Once the surgeon has fixed the scan area, he can verify that it is what he intended by instructing the laser system to scan using visible light. This allows the surgeon to preview the region to be scanned by the laser. If the scanned area is not appropriate, the surgeon can reposition the patient or adjust the range of the laser as described above.

In addition to being able to deliver uv laser energy sufficient for tissue ablation at these locations, the system can illuminate the area to be treated with light visible to the human eye or to an electronic detector or imaging detector array. This visible light serves to align the system by illuminating the tissue at the same location where the ablating uv beam strikes the tissue, when the uv is not otherwise shuttered or turned off. Alternatively, the system can be a two degrees of freedom (2DOF) robotic device that can accurately and repeatably scan a laser beam over a designated area of skin. The system could be a 2DOF robotic arm with a laser beam emerging from the delivery end.

In the following versions of the present invention, the robot/laser system can be programmed to: (i) systematically visit every location within a designated area in succession (full raster scan); (ii) visit only certain locations of interest on the skin surface; or (iii) perform a full raster scan with the exclusion of certain designated regions within the full area being scanned. For each of these scenarios, the general procedure is to alternate between (a) designating regions of tissue to be irradiated and (b) exposing these regions of interest to laser energy, thereby removing a thin layer of tissue, with steps (a) and (b) being repeated until the treatment is complete.

Scenario (i): systematically visiting every location in succession, while protecting certain locations from tissue ablation by use of a physical mask. Referring again to FIG. 4A, the robot/laser system 400 is capable of emitting two different laser beams, a uv radiation laser for ablation and a visible laser for alignment. With the uv radiation laser source shuttered, the surgeon scans the visible alignment beam 412 across the area of skin to be treated, thereby designating the area for the system control mechanism. The surgeon then applies a physical mask or masking material 410 to those regions 406 within the area that will be illuminated during the ablation scan but which are not to receive treatment, i.e. not to be ablated. The mask might be made of a reflective material, thereby directing the uv laser energy away from the underlying skin. Alternatively, it could be made of an absorbing material with a threshold for ablation greater than that of skin. Yet another alternative is the absorbing material might be of sufficient thickness that the process does not erode all the way through the mask. Next, the surgeon opens the shutter, admitting the uv radiation and uses that radiation to scan the designated area 407. Following a full scan, the surgeon assesses the irradiated area. A masking material can then be applied to those regions where no more tissue should be removed. The surgeon then repeats this process until all locations to be treated have been ablated to the desired depth, with the masked-off region expanding with each iteration. Since the locations to be ablated are distinguished by a physical mask from the adjacent locations that are not to be ablated, minor patient motion can be tolerated during all phases of the procedure.

Scenario (ii): visiting only certain locations within the larger area to be treated, protecting other locations within that larger area from ablation by an "electronic shutter." FIG. 4C depicts an example of a computer-controlled robot/laser system 402 in accordance with the present invention capable of emitting two different laser beams: a uv radiation laser for ablation; and a visible laser for alignment. The surgeon can, as before, designate the locations to be ablated by using an alignment light 412 to define these locations. The alignment light can be pointed and moved to outline the locations of skin to be treated. Additionally, a phosphorescent material can be applied to make the outlined region easier to read. An input device 450 such as a joystick, mouse, or force-torque sensor, can be used to translate the surgeon's hand motion into motion commands for servo motors controlling the visible beam position. It is well known in the art of computer-integrated surgery to record in a computer the specific point locations on or in a patient using a multitude or variety of 3D localizing technologies, e.g., mechanical pointing devices. See e.g., *Computer-integrated Surgery: Technology and Clinical Applications*, Russell H. Taylor et al., (editors), The MIT Press, pp. 5–19,(1996) (hereinafter "Computer Surgery"). According to the present invention, a robot/laser system preferably includes computer software for recording the visible beam positions which have been designated by the surgeon for subsequent "playback" using the ablating laser. In essence, the surgeon outlines the locations to be ablated directly on the patient's skin by using the visible light beam as a "drawing" tool.

A complete procedure may involve many iterations. As an initial step, the surgeon can use the visible light 412 to position the system. The area of interest 455 can then be outlined. At this point, these locations can be previewed in visible light or the system switched to ablation mode and directed to deliver controlled treatment of these locations. Note that the patient should not move from the time the surgeon designates the locations of interest to the time the ablation scan is completed. The patient is then free to move. For the next iteration, new areas of interest can be designated, which may or may not overlap the previous locations, and the process repeated. This procedure is repeated for as many times as it takes to ablate all of the designated locations of skin to the desired depths. The surgeon is typically making decisions from iteration to iteration.

In many cases, the area being treated can require many iterations to attain the full treatment and if the patient moves between iterations, the treatment region must be re-designated by the surgeon. This may become tedious, slow and lead to inaccurate treatment. Thus, it is desirable to develop a registration, well known in the art, between the area of treatment on the patient and the coordinate frame of the robot (see e.g., Computer Surgery, pp. 75–97). A more detailed example of a registration technique in accordance with the present invention follows in scenario (iii), but briefly, the region can be registered to the patient by determining the three-dimensional (3D) position of the area of skin surface to be treated. This surface area is then tracked when the patient moves. The result is that a location of treatment designated by the surgeon can be identified by the system, from iteration to iteration, even though the patient moves, without active re-designation by the surgeon. This same capability allows the surgeon to build up a complicated pattern of treatment over successive iterations. For example, the surgeon can re-irradiate a region of locations previously irradiated with the additional specification of a region within the larger region that will be "electronically masked off."

Figure 5:
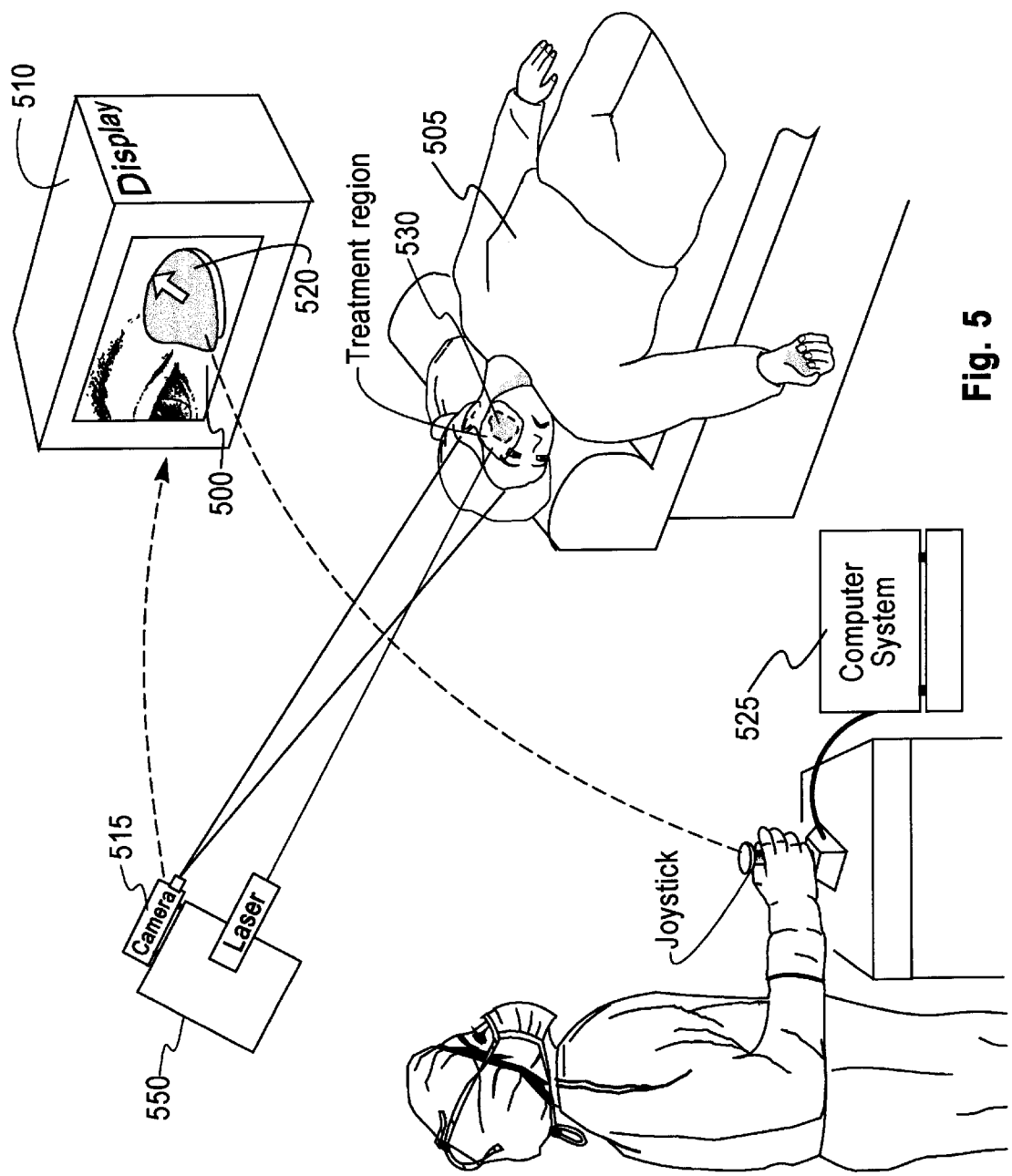
FIG. 5 depicts a form of the apparatus including the surgeon interacting with the patient via a remote mechanism in accordance with the present invention.

Scenario (iii): systematically scanning an ablating uv laser over an area while automatically "shuttering" the laser when certain locations (for which no further ablation is desired) are in the target area. FIG. 5 depicts an example of a computer assisted UV Dermablator system having features of the present invention. As depicted, a surgeon can designate locations of interest on a digital image 500 of a patient 505 on a computer display 510, rather than directly on the patient. This will make the region-editing functions easier to use. A camera 515 can be mounted on the system such that the area of skin to be treated is within its field of view. The system is preferably configured so that a digital image is available to a computer 525 for display, image processing, and interaction. To maintain a correspondence between the area designated in the camera image 500 and the area that will be scanned 530 by the ablating laser 550, these two areas must be registered with respect to one another. (Registration is described below).

By way of overview, the surgeon can use a visible alignment light to illuminate the patient and carry out a scan in order to get an appropriate initial placement of the system relative to the patient. The surgeon then records ("snaps") an image of the patient. Then, an automatic (or semiautomatic) registration can be performed to align the laser system with the camera image. Now the patient must not move until a scan with the ablating uv laser is complete. Using a mouse, joystick, or touch screen, the surgeon designates on the digital image the locations to be treated. Working with this digital image makes available the full graphics power of the computer to provide a richer pallet of editing techniques, such as area growing, area shrinking, inversion, outlining, color discrimination, etc. The surgeon can then treat the designated locations using the ablating laser. The patient may then move. The process is then repeated for additional iterations (snap image, register, designate locations, ablate) until the surgeon determines that treatment is complete.

Registration: Scenarios (ii) and (iii) can call for some sort of registration to relate the coordinates of a point in one coordinate frame of reference to its corresponding position in a different coordinate frame of reference. In scenario (ii), the points corresponding to an area of skin on the patient (in the patient's current position) may need to be related to the area of skin defined earlier (before the patient moved). In scenario (iii), an area of skin defined in a digital image must to be related to an area of skin on the patient, so that the ablating laser beam can be accurately aimed.

Figure 6:
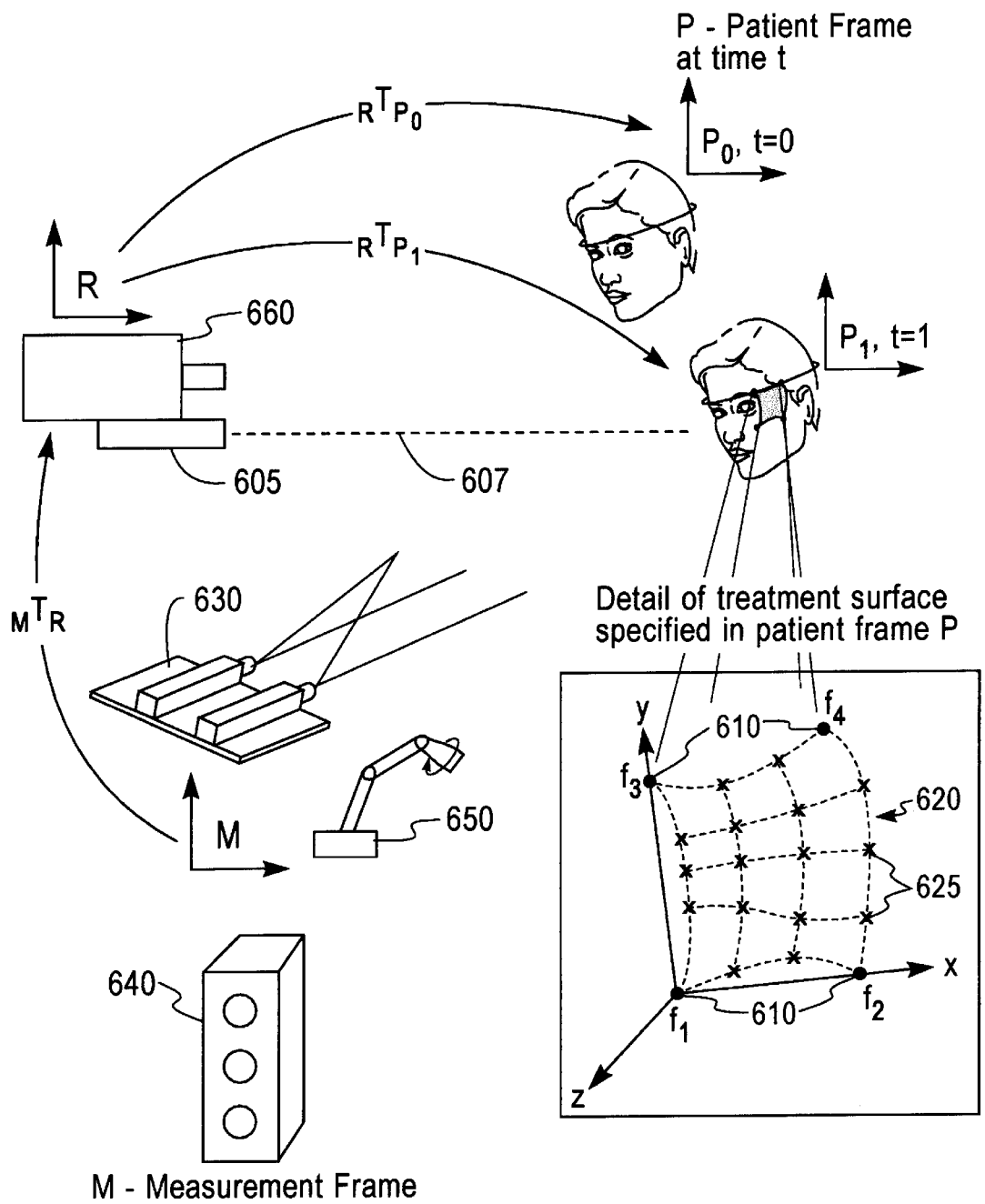
FIG. 6 is a diagram helpful in explaining the operation of the apparatus of FIG. 4C and FIG. 5.

Consider scenario (ii) with reference to FIG. 6, which depicts an example of the frames of reference and transformations between these frames of reference needed for registration in accordance with the present invention. To enable registration of an area of skin after patient movement with that same area of skin before movement, one first defines that area of skin with respect to a coordinate system "P" attached to the patient. That coordinate system is then reregistered by a visible tracking laser 605 mounted on the robot/laser system, relative to 660 the coordinate frame "R" associated with the robot/laser system. Such registration can be accomplished by attaching several markers, or fiducials 610, to the patient, pointing the tracking laser beam 607 at each fiducial while the tracking laser is in one mounting position, moving the tracking laser to a second mounting position, and repeating the pointing process, thereby establishing the 3D locations of each fiducial in R through triangulation. The use of robot-assisted surgery and in particular fiducial markers for registration is well known in the art. See e.g., Kazanzides, et al, "An Integrated System for Cementless Hip Replacement," IEEE Engineering in Medicine and Biology Magazine 14, pp. 307–313 (1995).

In greater detail, the patient coordinate frame P is defined in terms of the fiducials 610. This reference frame P is an orthonormal basis made up of the vectors x, y and z. For example, the x-axis of the patient coordinate frame P might be a vector formed by a line from a first fiducial $f_1$ to a second fiducial $f_2$, with $f_1$ serving as the origin of frame P. Additional fiducials might be placed at locations $f_3$ and $f_4$. With the 3D locations of the fiducials 610 established in reference frame R, Gram-Schmidt orthogonalization may be used to define y and z in terms of x and the coordinates of the fiducials 610 (in R). A description of this orthogonalization procedure is given in Edwards and Penney, Elementary Linear Algebra, pp. 241–242, Prentice-Hall, Englewood Cliffs, N.J., (1988). The transformation $_RT_P$ between the two frames of reference, P and R, can then be computed in a straightforward manner. Any time the patient moves, for example from position 0 to position 1, the patient frame changes from $P_0$ to $P_1$, and a new transformation $_RT_P$ can be established through triangulation.

The area of interest in the patient frame of reference is defined by constructing a surface 620 passing through the fiducials (the "fiducial surface"). When the surgeon identifies an area of interest with the tracking laser, this beam will intersect the fiducial surface 620 at a set of locations 625. The set of 3D points corresponding to these intersections is fixed in the patient coordinate frame P, even when the patient moves. So, to register an area of interest after the patient moves, only the transformation $_RT_P$ for the new position of the fiducials need be computed.

Registration in scenario (iii) with a camera recording digital images of the patient has many similarities to scenario (ii). Again, the area of interest is defined in terms of the patient coordinate frame P by the intersection of the alignment laser and a surface 620 constructed through the known fiducial positions 610 and the locations of intersection 625. The main difference is that the positions of the fiducials is determined by triangulation using two cameras 630 instead of using two different positions of a tracking laser. The cameras can be mounted at fixed positions relative to the robot/laser frame 660. Their position (the measurement frame "M") relative to the robot/laser frame 660 is known from a calibration transformation $_MT_R$ determined prior to the medical procedure and does not change in the course of this procedure. Those skilled in the art will appreciate that alternatively, one camera could be used by moving it to two different positions. An accurate camera model has preferably also been built prior to the procedure, so that the relationship is known between each location (pixel) in the 2D camera image and the set of 3D points (within a cone) that map to it. Given this camera model, when the surgeon snaps the images, a pair of stereo images is captured and made accessible to a computer (not shown). Well known image processing techniques can be used to identify the fiducials 610 and to establish the coordinate axes (x,y,z) of the patient frame of reference P. Ambiguity in establishing the correspondence between fiducial images in the pair of camera images (e.g., if one fiducial is obscured by the second fiducial in one image of the pair while both fiducials give distinct points in the second image) may be resolved by the surgeon based on his visual observation of the patient. (See e.g., D. H. Ballard and C. M. Brown, Computer Vision (Prentice-Hall, Englewood Cliffs, N.J., 1982), pp. 88–93). The surgeon can then designate an area of interest directly on one of the images on a computer screen, as described above. As in the registration scenario (ii), the system translates this designation into the area of interest in the patient frame P. The system is then capable of following this surgical plan, i.e. determining the set of robot/laser ablation locations that correspond to the region designated on the screen.

Alternative means to using the cameras 630 for locating the fiducials 610 include the use of a 3D digitizer 640 (an array of cameras that optically tracks light-emitting diode markers affixed to the patient), e.g., an OPTOTRAK™ device (manufactured be Northern Digital, Inc., Canada) (see. e.g. R. H. Taylor et al, "An overview of computer-integrated surgery at the IBM Thomas J. Watson Research Center," IBM J Research and Development 40, p. 172 (1996)) or of a calibrated pointing device 650 (a mechanically manipulated pointer to reach out and point to the fiducials 610), e.g., the VIEWING WAND™ (manufactured by ISG Technologies, Inc., Canada).

Several safety features can be built into the UV Dermablator. The surgeon makes the decision as to which area of skin to treat and how many pulses of light are to fall on each location of tissue. He can then set the robot/laser system on "automatic pilot." But the surgeon will be watching the procedure and can intervene at any time, taking "manual" control of the system. This is analogous to putting an automobile in cruise control once a cruising speed is selected, but having the ability to instantly take back control by touching the brake pedal.

Also, insofar as a computer is being used to control the delivery of ablating energy to the patient's skin, each location of skin being irradiated can be labeled and its history recorded by the computer. Then, with a safety threshold set in advance, the system will not deliver pulses in excess of that threshold without an explicit command by the surgeon.

Figure 7:
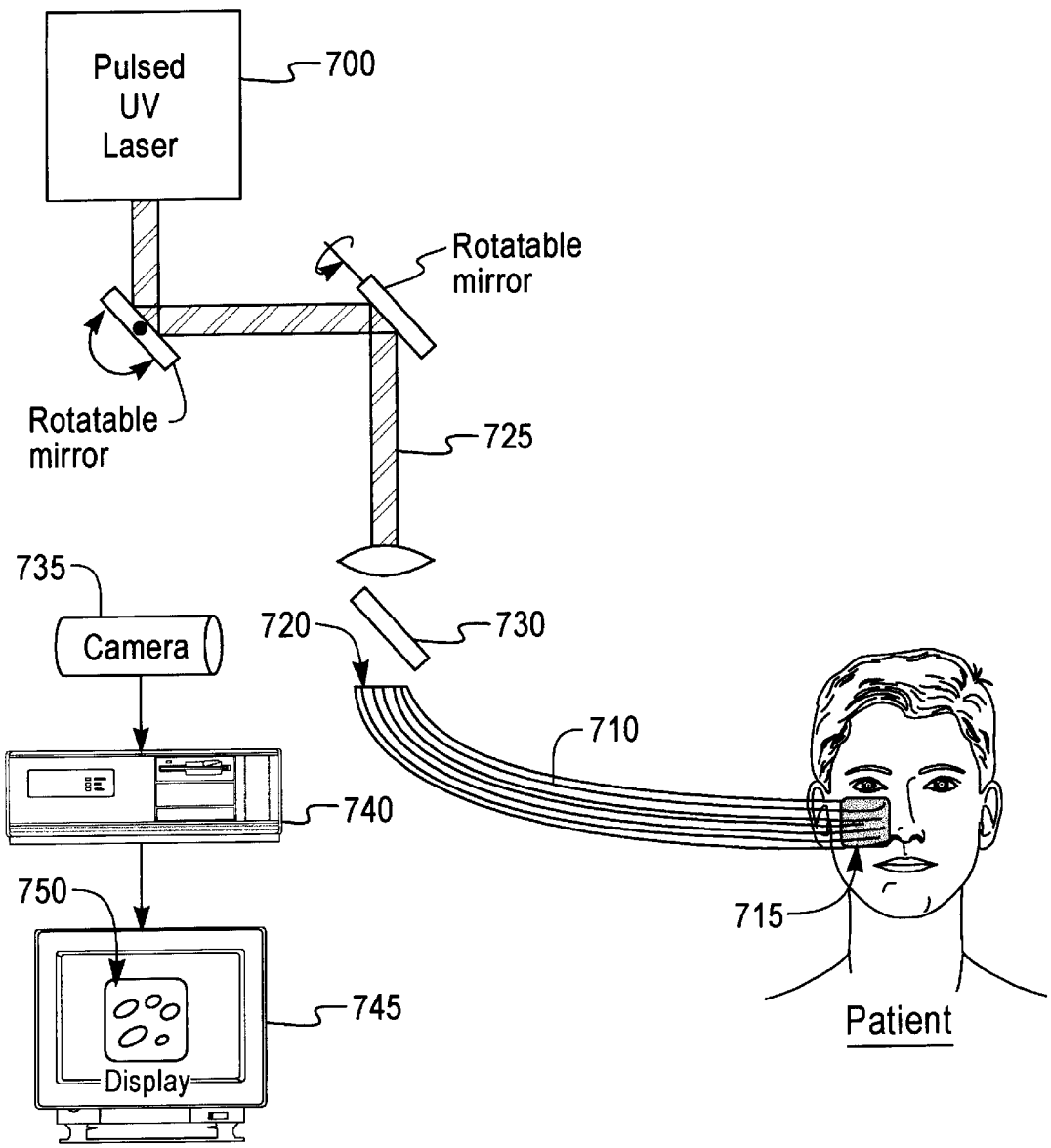
FIGS. 7–10 depict examples of an apparatus constructed in accordance with the present invention.

FIG. 7 depicts an example of an alternative system in accordance with the present invention for delivering laser energy to the patient's skin while permitting the patient to move throughout the procedure. As depicted, the system includes an optical fiber bundle 710, one end of which is clamped to a mask 715 worn by the patient while the other end, the input end 720, is scanned by an ablating laser beam 725 in a predetermined manner. The fiber bundle 710 is preferably flexible and abuts the patient's skin. The surgeon can look at the skin through the input end 720 of the fiber bundle 710, using, for example, a mirror 730 that snaps into position for viewing. This mirror 730 snaps out of the way for ablation, working like the mirror in a single lens reflex (SLR) camera. With the viewing mirror in place, a camera 735 can view the patients skin, deliver its image 750 to a computer 740 and computer display 745, and the surgeon can mark the areas to be treated as described in scenario (iii). With the viewing mirror 730 displaced, the ablation can proceed, the laser 700 scanning across the input end 720 of the fiber 710 in a predetermined pattern. Successive viewing, marking, and ablation iterations are carried out until the procedure is completed to the surgeon's satisfaction. Use of this fiber bundle 710 eliminates the need for re-registration between each iteration, because the output end of the bundle does not move relative to the patient during the procedure.

Process—UV Dermablation: The ablation of skin by pulsed uv light in accordance with the present invention can remove epidermal tissue with minimal damage to the underlying dermis and minimal scar tissue and erythema. Since each pulse of uv light removes less than a cellular layer of tissue, it is possible to control the procedure with great precision, ablating the skin to the desired depth and no more.

In a preferred embodiment, the skin is ablated to a depth where bleeding just commences, with no deeper penetration. So a process is needed to stop the ablation as soon as bleeding is detected.

Alternatively, the process can be slowed at the first hint of bleeding and brought to a complete halt at an additional, adjustable predetermined depth, depending on the patient's skin condition. Referring again to FIG. 1A, the dermis, which is much thicker than the epidermis (up to 4 mm thick), has fewer cells, and is mostly connective tissue or fibers. Blood vessels course through the dermis. The skin is vastly perfused with blood. The mean blood flow is many times greater than the minimum flow necessary for skin cell nutrition because cutaneous blood flow serves as a heat regulator of the entire organism. Thus blood is plentiful and flowing at depths just below the basement membrane. Once the ablation process perforates a capillary wall, blood will perfuse into the incision.

For the purposes of this invention, blood differs from the surrounding dermis in one very important way: the aqueous chlorine ions in blood are a strong absorber of uv radiation at wavelengths below 200 nm, with an absorption maximum at 190 nm. This absorption differs from the absorption of uv light by cells and protein molecules in that the absorbed energy is not quickly degraded into heat. So the "salt water" that is the major component of blood will "block" the incoming uv light and attenuate or completely halt the ablation process, depending on how much blood is pooled in the cavity of the incision (The uv photon energy detaches an electron from the chlorine ion, leaving a chlorine atom and a solvated electron dissolved in the water. Eventually, on a time scale long compared to ablation and thermal diffusion times, the electrons will encounter neutral chlorine atoms and recombine to form ions, giving up the photodetachment energy to heat, but the temperature rise will be minimal and of no consequence to the viability or morphology of the tissue (see e.g., R. J. Lane, R. Linsker, J. J. Wynne, A. Torres and R. G. Geronemus, "Ultraviolet-Laser Ablation of Skin," Archives of Dermatology 121: 609–617 (1985); and E. Rabinowitch, "Electron Transfer Spectra and Their Photochemical Effect," Reviews of Modern Physics 14: 112–131 (1942)). One way to take advantage of this effect is to horizontally orient the skin surface being treated, and direct uv radiation in the spectral region of the photodetachment energy, e.g., an ArF laser radiation at 193 nm, at the target surface from above. As blood perfuses the incision, it will pool under the influence of gravity, and act as a "block" against further tissue ablation. Alternatively, the patient can sit in a comfortable position and the punctate blood spots that appear when capillary walls are penetrated will serve to block further ablation of tissue under the punctate blood. Since the skin being treated varies in thickness, different regions of the skin will start to bleed at different depths of penetration, but the naturally occurring bleeding will block ablation at an appropriate depth for each region of skin.

At various points in the Dermablation procedure, it will be desirable to remove the blood or stem the bleeding, to prevent the region of treatment from being obscured. Blood can be washed away with physiologic saline solution, but such solution will continue to act as a "block" against further ablation by uv radiation in the photodetachment energy spectral region, e.g., the ArF excimer laser at 193 nm. The bleeding area can also be washed by deionized water, which is transparent to radiation at the uv wavelengths of the ArF, KrF, XeCl, and XeF excimer lasers.

Figure 8:
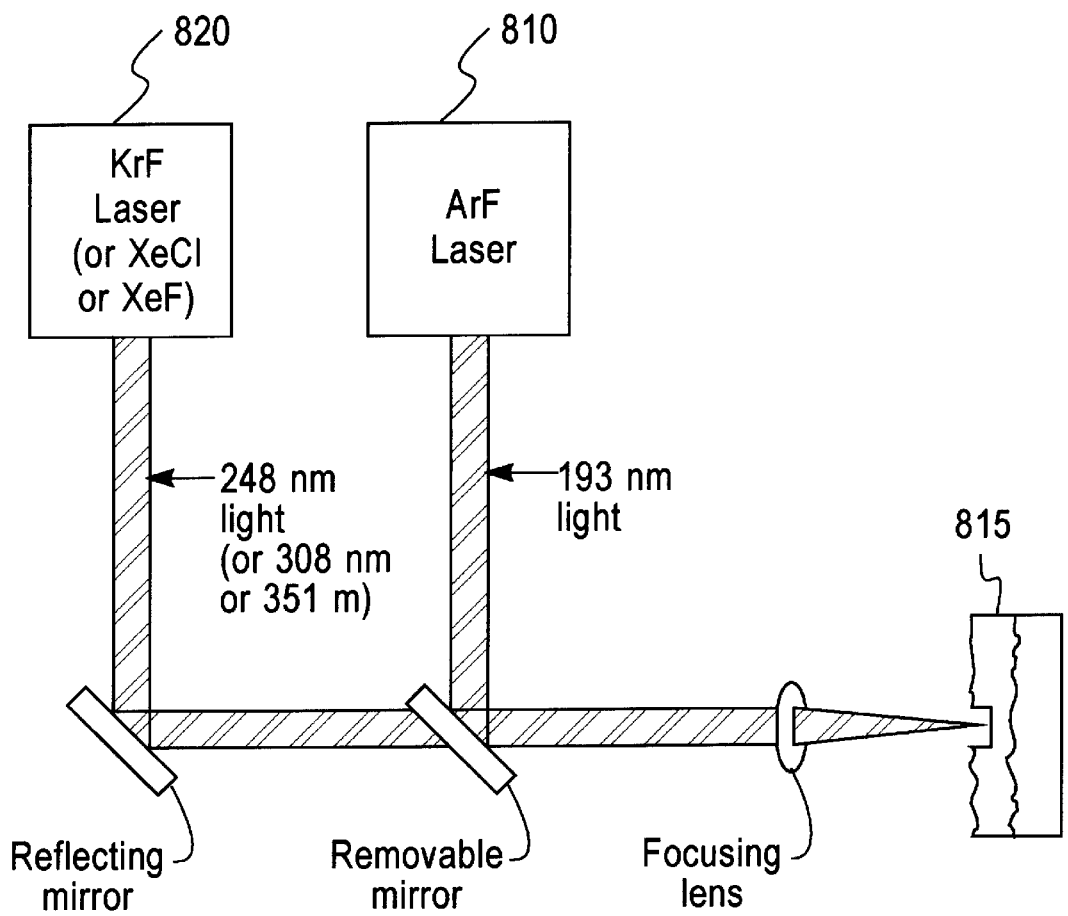

FIG. 8 depicts a dual laser system having features of the present invention. As depicted, first 193 nm radiation from an ArF laser 810 can be used to ablate the skin 815 until bleeding blocks the ablation. Next the wavelength is changed (by, for example, using a second laser 820 supplied with a gas mixture producing longer wavelength light, such as KrF, XeCl or XeF) so that the radiation at the second wavelength will not be blocked by photodetachment, but will be absorbed by blood protein, heating it sufficiently to coagulate the blood. Thus, further bleeding is stemmed, yet the tissue retains an intact ability to heal without the formation of scar tissue.

Figure 9:
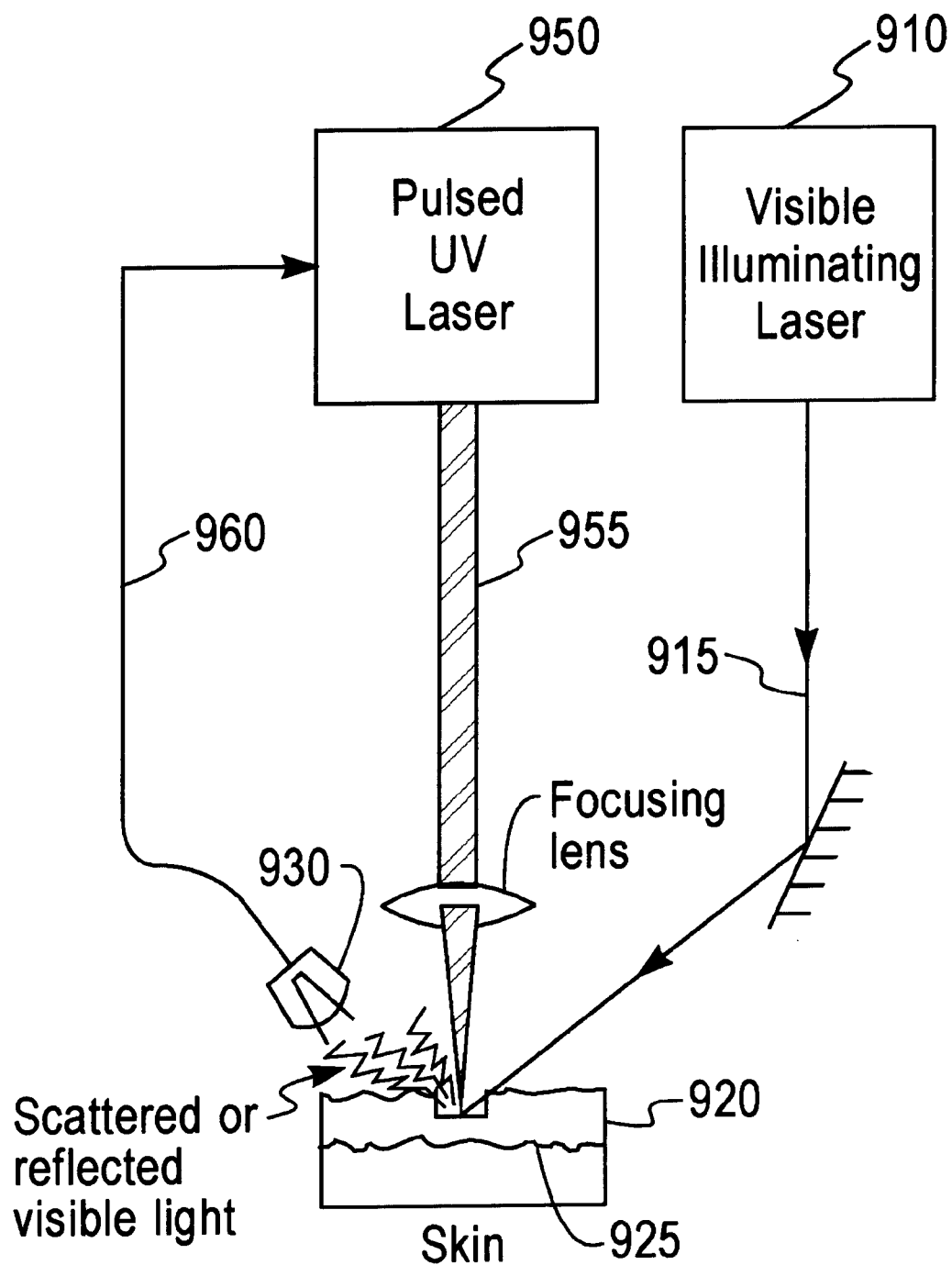

FIG. 9 depicts another example of a system in accordance with the present invention. As depicted, evidence of bleeding can be detected using a visible illuminating laser 910 that is aimed at the skin to overlap the uv radiation 955, this visible beam 915 scattering from the rough surface of the skin being treated to form a visible "spot" that can be detected by the practitioner's eye or by a photodetector 930 mounted near the tissue being treated. When punctate blood appears, a small fraction of the visible laser beam will reflect specularly from the surface of the liquid and a major fraction of the visible laser beam will be absorbed by the pigment (hemoglobin) in the red blood cells in the blood, leading to a great reduction of the light hitting the photodetector. This reduction in signal can be fed back to the uv laser 950 power supply or to a beam shutter by a control signal 960 which terminates the surgical procedure.

Alternatively, instead of penetrating into the papillary dermis to a depth sufficient to induce bleeding, the complete ablation of the epidermis can be detected by monitoring for the first appearance of the white dermal boundary 925. The dermis is first revealed when the pigmented epidermis and basal cells are totally removed. For example, a focused laser beam 955 of small cross section (compared to the area of a papillae or rete ridge) can be scanned and shuttered in response to detecting white dermal tissue 920. Such color change can be detected visually by the medical practitioner's eye. Alternatively, the color change can be detected by the photodetector 930 monitoring the amount of scattered light from the visible laser beam 915. To improve the ability to detect the color change in the presence of ambient lighting, the photodetector 930 might be equipped with a filter tuned to the color of the illuminating visible laser beam 915. By limiting the detected light to the narrow spectral region around the color of the visible laser, the detection scheme discriminates against ambient light at all other colors, thereby improving the precision with which the appearance of the dermal boundary can be detected and used for feedback to terminate the surgical procedure.

Figure 10:
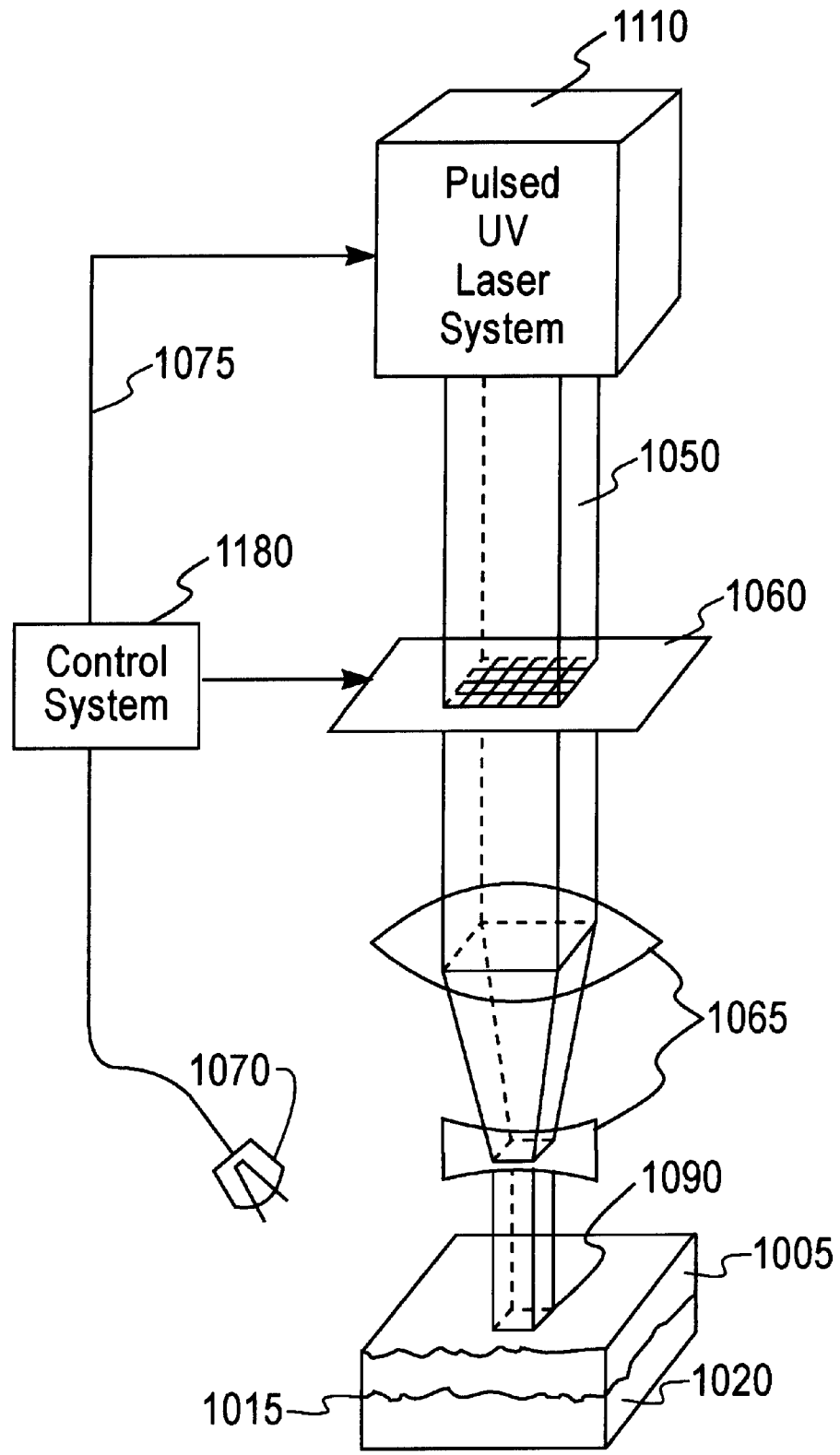

FIG. 10 depicts another example of a laser system having features of the present invention. As depicted, a laser system 1010 can apply a laser beam 1050 over a relatively large area, encompassing many papillary contours. An active mask 1060 between the source 1010 of the beam and the skin, can be used to shutter selected areas of the beam (FIG. 10). The mask 1060 could be controlled by a detector 1070 or an array of detectors, so that each area of the skin being irradiated can provide a color-change based feedback signal 1075 to a control system 1080 which then inhibits or shutters a section of the laser beam irradiating that area, in a one-to-one "map." Recall that the epidermis 1005 contains melanin while the dermal layer 1020 is white. This mask could be controlled electro-optically, or even be mechanically shuttered by an array of opaque flaps that rotate into the beam so as to block selected areas. The mask 1060 might be placed in the ablating laser beam 1050 at a location where the beam is relatively defocused, covering a large area. At such a location the laser beam 1050 will be of such low intensity and low fluence so as not to damage the mask. At this location, each element of the array can be relatively large. When the beam is focused by projection lenses 1065 to a smaller area 1090 on the skin, the light passing through each element will be correspondingly demagnified as well as intensified. In this way the pattern of light transmitted by the mask array may be projected to a correspondingly smaller area on the skin, yielding a transverse precision suitable for following the contours of the epidermal/dermal boundary. In addition, the focusing increases the fluence of the laser beam, ensuring that it is above threshold for ablation. In this way, the epidermis 1005 can be controllably ablated right down to the dermal boundary with great depth precision and transverse control, despite the irregular contours of the dermal/epidermal interface 1015.

In one embodiment, the photodetector 1070 could be used in conjunction with and responsive to an illuminating laser 910, as depicted in FIG. 9. It is known that the skin can be modeled macroscopically as a multilayered optical system (see The Science of Photomedicine, edited by James Regan and John Parrish, Plenum Press, N.Y., (1982), Chapter 6, pp. 147–194, which is hereby incorporated herein by reference in its entirety). The relation between sunburn protection and the degree of melanin pigmentation in the skin is well known. This is because melanin, which is present in the epidermis and is most concentrated in the basement membrane, is a strong absorber of both shorter wavelength visible light and UV radiation. In the spectral region approximately from 350 nm to 1300 nm (which includes the near UV from 350 nm to 400 nm, the visible from 400 nm to 700 nm, and the near infrared from 700 nm to 1300 nm), the epidermis can be modeled generally as an optically absorbing element while the underlying dermis acts as a diffuse reflector whose remittance increases with the wavelength. The epidermal remittance in this region is essentially due to the regular reflectance at the surface of the skin (~5% for a normally incident beam). A change (as detected by photodetector(s) (930, 1070)) in the remittance of an external (UV, visible or infrared) illuminating laser, resulting from the complete removal of the melanin-containing epidermis, could be fed back to selectively shutter the UV laser or the active mask 1060. For example, the illuminating laser might be scanned across the area being ablated through the mask array 1060, illuminating in sequence each area corresponding to the projected image of one of the elements of the mask array. Scattered light detected by photodetector 1070 could then provide the feedback signal 1075 to shutter the laser beam selectively at the locations of the mask array that project to the areas of skin that have been ablated to the desired depth. By way of example only, it is known that at 330 nm–400 nm and 650–700 nm, melanin is highly absorptive while dermal absorption is negligible. The photodetector would be selected to transmit its control signal in response to an increase (or decrease) in remittance for the wavelength of an illuminating laser emitting light in one of these spectral regions.

Melanin, which is the pigment that colors the epidermis, originates from melanocytes in the basal cell layer. Once the basal layer is removed, a new basal layer must be regenerated in order to provide pigment to the overlying epidermis. If the skin is removed to such a depth that the hair follicles included in the region of removal are too badly damaged, they will fail to act as "seeds" for regeneration of a pigmented basal layer, and the healed region will appear to be much whiter (contain less melanin) than the surrounding skin. The UV Dermablation method and apparatus of the present invention advantageously provides such fine depth control that the hair follicles will be spared from destruction, remaining viable and capable of acting as a source for regeneration of a fully functional basal layer, including fresh melanocytes capable of providing a pigmentation that matches the surrounding skin.

In the application of UV Dermablation to remove basal cell carcinomas, the skin to be treated can be first stained by an exogenous agent, a chemical such as those used for histological preparation of biopsy specimens. This will "mark" the lesion with a coloration and darkness that will provide contrast to surrounding healthy tissue. Then the scheme of FIG. 9 can be used to control the dermablation process, with a visible laser beam illuminating the tissue at the point of ablation, the scattered visible light being measured to determine if that point has lesion tissue or healthy tissue at the surface, and this measurement being used to control the shuttering of the uv beam when healthy tissue is at the point of irradiation. A scan can be taken over a designated area containing the basal cell carcinoma, and this scan can be repeated for a sufficient number of iterations until the lesion is entirely removed, as determined by the measurement signal derived from the scattered visible light.

What is claimed is:

1. A surgical system for removing skin, comprising:
   a pulsed light source capable of delivering a fluence F exceeding an ablation threshold fluence $F_{th}$;
   a second light source illuminating the skin;
   a control mechanism, coupled to the pulsed light source, for directing light from the pulsed light source to locations on the skin and controllably ablating a skin location to a desired depth, said control mechanism directing the pulsed light source to deliver multiple pulses of directed light at the locations on the skin and repeatedly scanning the directed light across a designated area of the skin; and
   a feedback mechanism coupled to the control mechanism, the feedback mechanism comprising at least one photodetector having an input and an output: the input receiving light from the second light source that is scattered/reflected/flouresced by the skin; and the output providing a feedback signal to the control mechanism, which is adapted for detecting a change in the spectral shape or brightness of the light scattered/reflected/flouresced by the skin and causing the pulsed light source to be inhibited at a given skin location, in response to the change.

2. The system of claim 1 wherein the light source is an ultraviolet light source.

3. The system of claim 1 wherein the light source is a laser selected from a group consisting of: an argon fluoride (ArF) laser having a wavelength of approximately 193 nm; a krypton fluoride (KrF) laser having a wavelength of approximately 248 nm; a xenon chloride (XeCl) laser having a wavelength of approximately 308 nm; a xenon fluoride (XeF) laser having a wavelength of approximately 351 nm; and an Er:YAG laser.

4. The system of claim 1 wherein the control mechanism comprises means for controllably ablating the epidermis along the contours of an epidermal/dermal boundary.

5. The system of claim 4 wherein said means for controllably ablating further comprises means for detecting a color change near or at the epidermal/dermal boundary.

6. The system of claim 1, wherein the second light source comprises a visible light source.

7. The system of claim 1, wherein the second light source comprises an infrared light source.

8. The system of claim 1, wherein the second light source comprises ambient light source.

9. The system of claim 1, the second light source comprising a light source which is both relatively highly absorbed by epidermal melanin and relatively highly remitted by a dermal layer.

10. The surgical system of claim 1 wherein the light source is a laser wherein the system further comprises a mechanism for focusing the laser beam to a small spot approximately ~25 µm in diameter.

11. The system of claim 1, wherein the second light source provides an inhibiting signal to the feedback mechanism for inhibiting the pulsed light source in response to the appearance of blood following a delivery of directed light from the pulsed light source.

12. In a surgical system including a pulsed light source capable of delivering a fluence F exceeding an ablation threshold fluence $F_{th}$, a method for removing skin, comprising the steps of:
    directing light from the pulsed light source to locations on the skin;
    delivering, from the pulsed light source, multiple pulses of directed light at the locations on the skin;
    repeatedly scanning the directed light across a designated area of the skin;
    receiving from a second light source, light that is scattered/reflected/flouresced by the skin;
    detecting a change in the spectral shape or brightness of the light scattered/reflected/flouresced by the skin; and
    controllably ablating a given skin location to a desired depth by inhibiting the pulsed light source at the given skin location, in response to the change.

13. The method of claim 12 wherein the light source is an ultraviolet light source.

14. The method of claim 12 wherein the light source is a laser selected from a group consisting of: an argon fluoride (ArF) laser having a wavelength of approximately 193 nm; a krypton fluoride (KrF) laser having a wavelength of approximately 248 nm; a xenon chloride (XeCl) laser having a wavelength of approximately 308 nm; a xenon fluoride (XeF) laser having a wavelength of approximately 351 nm; and an Er:YAG laser.

15. The method of claim 12 wherein said controllably determining step comprises the step of controllably ablating the epidermis along the contours of an epidermal/dermal boundary.

16. The method of claim 12 wherein said controllably determining step further comprises the step of detecting a color change near or at the epidermal/dermal boundary.

17. The method of claim 12, wherein the second light source is selected from a group consisting of: a visible light source; an infrared light source; and an ambient light source.

18. The method of claim 12, wherein the second light source is both relatively highly absorbed by epidermal melanin and relatively highly remitted by a dermal layer.

19. The method of claim 12, wherein said inhibiting step further comprises the step of inhibiting the pulsed light source at a given location, in response to the appearance of blood.

* * * * *